United States Patent [19]

Hunkeler et al.

[11] 4,352,817
[45] Oct. 5, 1982

[54] IMIDAZO-DIAZEPINES AND THEIR USE

[75] Inventors: Walter Hunkeler, Magden; Emilio Kyburz, Reinach, both of Switzerland

[73] Assignee: Hoffmann-La Roche Inc., Nutley, N.J.

[21] Appl. No.: 349,802

[22] Filed: Feb. 18, 1982

[30] Foreign Application Priority Data

Feb. 27, 1982 [CH] Switzerland .................. 1340/81

[51] Int. Cl.³ .................. A61K 31/55; C07D 487/04; C07D 513/14
[52] U.S. Cl. .................. 424/273 R; 260/239.3 T; 260/239.3 B; 260/239.3 D
[58] Field of Search .............. 260/239.3 T; 424/273 R

[56] References Cited

U.S. PATENT DOCUMENTS 4,316,832   2/1982   Gerecke et al. .............. 260/239.3 T Primary Examiner—Robert T. Bond
Attorney, Agent, or Firm—Jon S. Saxe; Bernard S. Leon; Frank P. Hoffman

[57] ABSTRACT

There is provided imidazodiazepines of the formula

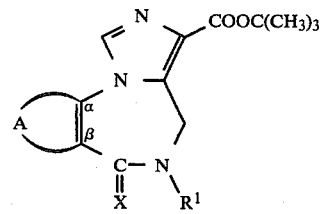

wherein A together with the two carbon atoms denoted as $\alpha$ and $\beta$ is the group

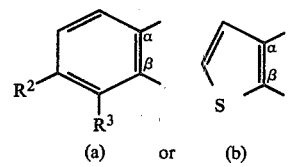

(a)   or   (b)

X is an oxygen or sulphur atom and $R^1$ is hydrogen or lower alkyl, and either $R^2$ is hydrogen, trifluoromethyl, halogen, cyano or nitro and $R^3$ is hydrogen or $R^2$ is hydrogen and $R^3$ is trifluoromethyl, halogen, cyano, nitro or lower alkyl, and their pharmaceutically acceptable acid addition salts. The compounds are useful in the antagonization of the central-depressant, muscle relaxant, ataxic, blood pressure-lowering and respiratory-depressant properties of 1,4-benzodiazepines which have tranquillizing activity, for example as antidotes in the case of intoxications with 1,4-benzodiazepines which have tranquillizing activity.

Also presented are methods to produce the above imidazodiazepines.

11 Claims, No Drawings

IMIDAZO-DIAZEPINES AND THEIR USE

DESCRIPTION OF THE INVENTION

The present invention is concerned with imidazodiazepines. More particularly, the invention is concerned with imidazodiazepines of the formula

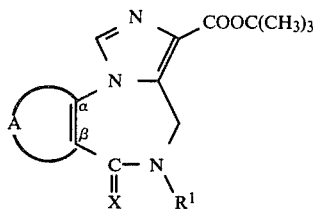

wherein A together with the two carbon atoms denoted as α and β is the group

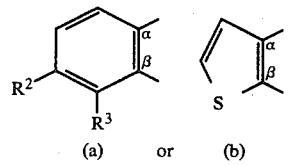

X is an oxygen or sulphur atom and $R^1$ is hydrogen or lower alkyl, and either $R^2$ is hydrogen, trifluoromethyl, halogen cyano or nitro and $R^3$ is hydrogen or $R^2$ is hydrogen and $R^3$ is trifluoromethyl, halogen, cyano, nitro or lower alkyl,
and pharmaceutically acceptable acid addition salts thereof.

These compounds are novel; they possess valuable pharmacodynamic properties and can be used in the control or prevention of illnesses.

Objects of the present invention are compounds of general formula I and pharmaceutically acceptable acid addition salts thereof per se and as pharmaceutically active substances, the manufacture of these compounds and intermediates for the manufacture of these compounds, medicaments containing a compound of formula, I or a pharmaceutically acceptable acid addition salt thereof and the manufacture of such medicaments.

The term "lower alkyl" denotes saturated hydrocarbon groups, which can be straight-chain or branched-chain, containing at most 7, preferably at most 4, carbon atoms such as methyl, ethyl, n-propyl, isopropyl, n-butyl, s-butyl, t-butyl and the like. The term "halogen" signifies fluorine, chlorine, bromine and iodine.

The symbol A preferably is group (a) in which preferably either $R^2$ is hydrogen or fluorine and $R^3$ is hydrogen, or $R^2$ is hydrogen and $R^3$ is chlorine, bromine, iodine or cyano. The symbol X preferably is an oxygen atom. $R^1$ preferably is methyl.

Especially preferred compounds of formula I are t-butyl 7-chloro-5,6-dihydro-5-methyl-6-oxo-4H-imidazo[1,5-a][1,4]benzodiazepine-3-carboxylate, t-butyl 5,6-dihydro-7-iodo-5-methyl-6-oxo-4H-imidazo[1,5-a][1,4]benzodiazepine-3-carboxylate and t-butyl 7-bromo-5,6-dihydro-5-methyl-6-oxo-4H-imidazo[1,5-a][1,4]benzodiazepine-3-carboxylate.

Other preferred compounds of formula I are:
t-Butyl 7-cyano-5,6-dihydro-5-methyl-6-oxo-4H-imidazo[1,5-a][1,4]benzodiazepine-3-carboxylate,
t-butyl 5,6-dihydro-5-methyl-6-oxo-4H-imidazo[1,5-a][1,4]benzodiazepine-3-carboxylate,
t-butyl 5,6-dihydro-5-methyl-6-thioxo-4H-imidazo[1,5-a][1,4]benzodiazepine-3-carboxylate and
t-butyl 8-fluoro-5,6-dihydro-5-methyl-6-oxo-4H-imidazo[1,5-a][1,4]benzodiazepine-3-carboxylate.

The imidazodiazepine of formula I and their pharmaceutically acceptable acid addition salts can be manufactured in accordance with the invention by
(a) reacting a compound of the formula

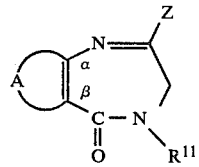

wherein $R^{11}$ is lower alkyl, Z is a leaving group, and A is as above,
in the presence of a base with the isocyanoacetic ester of the formula $$CN-CH_2-COOC(CH_3)_3 \quad \text{III}$$

or
(b) converting the carbonyl group in a compound of the formula

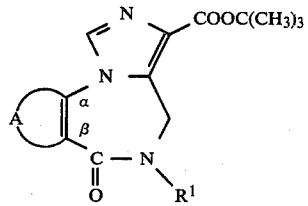

wherein $R^1$ and A are as above,
into the thiocarbonyl group, or
(c) converting a carboxylic acid of the formula

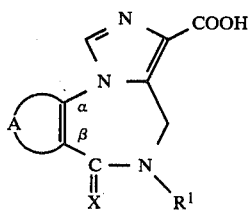

wherein A, $R^1$ and X are as above,
into the corresponding t-butyl ester, or
(d) appropriately substituting a compound of the formula

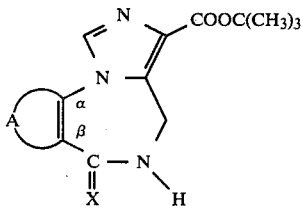

wherein A and X are as above,
at the secondary amino group, or
(e) replacing the halogen atom in a compound of the formula

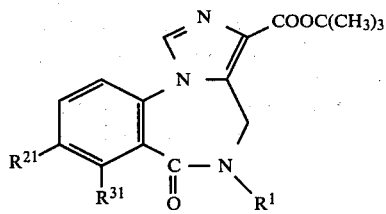

wherein one of $R^{21}$ and $R^{31}$ is halogen and the other is hydrogen and $R^1$ is as above,
by the cyano group, and
(f) if desired, converting a compound of formula I obtained into a pharmaceutically acceptable acid addition salt.

In accordance with process variant (a), compounds of formula I can be manufactured from compounds of formula II and the isocyanoacetic acid ester of formula III. The leaving group denoted by Z in formula II is, for example, a readily cleavable phosphinyl group, e.g., a group of the formula

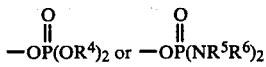

wherein $R^4$ is lower alkyl and $R^5$ and $R^6$ each are lower alkyl, allyl, phenyl or substituted phenyl or $R^5$ and $R^6$ together with the nitrogen atom are an unsubstituted or substituted heterocyclic ring with 3 to 8 members (such as morpholine),
a halogen atom, an alkylthio group, an aralkylthio group, a N-nitrosoalkylamino group, an alkoxy group, a mercapto group and the like (when Z is a mercapto group, then the corresponding compound of formula II is the iminothiol form of the corresponding thiolactam). The reaction of a compound of formula II with a compound of formula III is carried out in an inert solvent such as dimethylformamide, hexamethylphosphoric acid triamide, dimethyl sulphoxide, tetrahydrofuran or any other suitable organic solvent and in the presence of a base which is sufficiently strongly basic to form the anion of the isocyanoacetic ester of formula III. Suitable bases are alkali metal alkoxides such as sodium methoxide or potassium t-butoxide, alkali metal hydrides such as sodium hydride, alkali metal amides such as lithium amide or lithium diisopropylamide, tertiary amines such as triethylamine, and the like. The reaction is conveniently carried out at a temperature between about −40° C. and about room temperature.

In accordance with process variant (b), compounds of formula Ia can be converted into corresponding compounds of formula I in which X is a sulphur atom by treatment with a sulphurizing agent, which can be effected in a manner known per se. For example, the sulphurizing agent can be phosphorus pentasulphide, this being preferably used in excess and the reaction being advantageously carried out in an inert organic solvent such as dioxan, methylene chloride or the like in the presence of triethylamine at a temperature of about 50° C. up to the reflux temperature of the reaction mixture. Other suitable sulphurizing agents are compounds such as 2,4-bis(p-methoxyphenyl)-1,3,2,4-dithiaphosphetane-2,4-disulphide; such sulphurizing agents being used in approximately the calculated amount and the reaction being carried out in the presence of an inert solvent such as toluene or xylene, conveniently at the reflux temperature of the reaction mixture, or in hexamethylphosphoric acid triamide at a temperature between about 60° and 110° C.

In accordance with process variant (c), compounds of formula I can be manufactured by converting carboxylic acids of formula IV into the corresponding t-butyl esters. This esterification can be carried out according to methods which are known per se and familiar to any person skilled in the art. For example, a carboxylic acid for formula IV can be converted with a suitable reagent (e.g. thionyl chloride, phosphorus oxychloride, oxalyl chloride or the like) into the corresponding carboxylic acid chloride and this can be reacted with t-butanol in the presence of an acid-binding agent. Especially suitable acid-binding agents are tertiary amines such as triethylamine, pyridine, quinuclidine or the like. Under certain circumstances the presence of a catalytic amount of 4-dimethylaminopyridine or a similar reactive amine can be advantageous. This esterification can be carried out in two separate steps, i.e. formation of the reactive carboxylic acid derivative and reaction thereof with t-butanol, or in a so-called one-pot process, which is preferred. The reaction temperature conveniently lies in a range of about −10° C. to the boiling point of the reaction mixture.

In accordance with process variant (d), compounds of formula I can be manufactured by appropriately substituting compounds of formula Ib at the secondary amino group in the 5-position. This substitution is carried out according to methods known per se using an agent yielding one of the desired lower alkyl groups; for example, a corresponding organic sulphonic acid alkyl ester (e.g. p-toluenesulphonic acid methyl ester), a corresponding dialkyl sulphate such as dimethyl sulphate and diethyl sulphate, a corresponding alkyl halide such as methyl iodide, ethyl iodide or ethyl bromide, and the like. The compound of formula Ib is thereby conveniently used in the form of an alkali metal salt; this is conveniently achieved by allowing the reaction to proceed in the presence of a strong base or by converting the compound of formula Ib into an alkali metal salt before the reaction with the alkylating agent. Suitable bases are alkali metal alkoxides such as sodium methoxide or potassium t-butoxide, alkali metal hydrides such as sodium hydride, alkali metal amides such as lithium amide or lithium diisopropylamide, and the like. The reaction is conveniently carried out in the presence of an inert organic solvent. Suitable solvents for this purpose are, for example, dimethylformamide, dimethyl sulphoxide, ethyl acetate, lower alkanols and the like. Many other solvents and also solvent mixtures are also suitable and their choice presents no difficulties to a person skilled in the art. The reaction temperature can be varied within fairly wide limits and generally lies between about room temperature and about the boiling point of the reaction mixture.

In accordance with process variant (e), compounds of formula I in which $R^2$ or $R^3$ is cyano can be manufactured by replacing the halogen atom in compounds of formula Ic by the cyano group. In this case, a corresponding bromo or iodo compound of formula Ic is preferably used as the starting material. The reaction can be carried out, for example, by reacting the compound of formula Ic in an inert organic solvent with copper (I) cyanide. Suitable solvents are, for example, dimethylformamide and the like. The reaction temperature conveniently lies in a range of about room temperature to the boiling point of the reaction mixture.

In accordance with process variant (f), compounds of formula I can be converted into pharmaceutically acceptable acid addition salts. The manufacture of such pharmaceutically acceptable acid addition salts is carried out according to generally usual methods. The salts provided by the present invention are salts formed with inorganic acids and with organic acids; for example, hydrochlorides, hydrobromides, sulphates, methanesulphonates, p-toluenesulphonates, oxalates and the like.

The compounds of formula II used as starting materials can be prepared starting from compounds of the formula

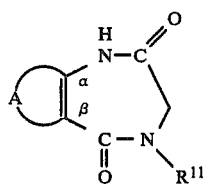   V wherein A and $R^{11}$ are as above,
according to methods which are known per se; see, for example, Belgian patent specification Nos. 802,233; 833,249 and 865 653, American Pat. No. 3,681,341 and J. Org. Chemistry 29, 231 (1964) which are incorporated herein for reference.

Various Examples hereinafter contain detailed information concerning the preparation of compounds of formula II from compounds of formula V.

The compounds of formula V, in turn, are known or can be readily prepared according to methods known per se; for example, by reacting a corresponding carboxylic acid anhydride of the formula

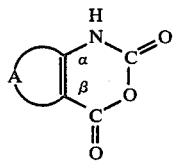   VI wherein A is as above,
with an amino acid of the formula $R^{11}$—NH—CH$_2$—COOH   VII wherein $R^{11}$ is as above.

The compounds of formula V can, however, also be prepared starting from compounds of the formula

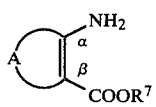   VIII wherein $R^7$ is lower alkyl and A is as above,
for example by treating such a compound with a reactive derivative of an α-haloacetic acid (e.g. α-chloroacetyl chloride) and reacting the intermediate obtained with a lower alkylamine such as methylamine, ethyl-amine and the like. There are thus obtained compounds of the formula

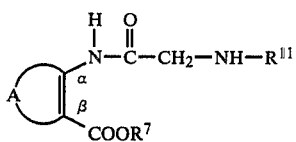   IX wherein A, $R^{11}$ and $R^7$ are as above,
By cyclizing compounds of formula IX there are obtained compounds of formula V. This cyclization is carried out, for example, by heating a corresponding compound of formula IX for a short time to a temperature of about 100° to about 300° C.

It is also possible to react a compound of formula VIII with a reactive derivative of a carboxylic acid of the formula

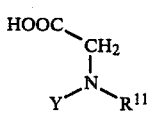   X wherein Y is a protecting group and $R^{11}$ is as above, for example a carboxylic acid chloride or the like. After removal of the protecting group denoted by Y from a thus-obtained compound of the formula

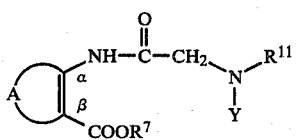   XI wherein A, $R^{11}$, $R^7$ and Y are as above,
and cyclization, in analogy to the preparation of compounds of formula V from compounds of formula IX, there is obtained a compound of formula V.

The compounds of formula IV used as starting materials can be prepared readily by hydrolyzing the ester group in compounds of the formula

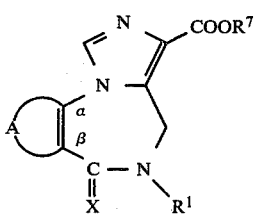   XII wherein A, $R^1$, $R^7$ and X are as above,
according to methods which are known per se and familiar to any person skilled in the art.

Compounds of formula XII in which $R^1$ is lower alkyl can be prepared by reacting a compound of formula II in the presence of a base with an isocyanoacetic ester of the formula

CN—CH$_2$—COOR$^7$   XIII wherein $R^7$ is as above,
[in analogy to process variant (a)], and, if desired, converting the carbonyl group in the product obtained into the thiocarbonyl group [in analogy to process variant (b)].

Compounds of formula XII in which $R^1$ is hydrogen can be prepared by reacting a compound of the formula

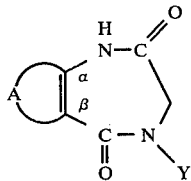

XIV wherein A and Y are as above,
with an isocyanoacetic ester of formula XIII in analogy to process variant (a) and cleaving off the protecting group denoted by Y in the resulting compound of the formula

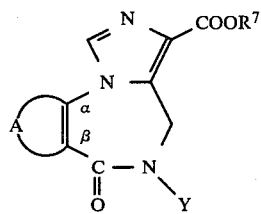

XV wherein A, $R^7$ and Y are as above,
and, previously or afterwards, converting the carbonyl group into the thiocarbonyl group.

In this case there come into consideration only protecting groups which can be cleaved off under mild acidic conditions, for example using dilute aqueous mineral acids such as dilute hydrochloric acid or dilute sulphuric acid, trifluoroacetic acid or the like, optionally with addition of a solubilizer such as tetrahydrofuran, dioxan, acetic acid, N,N-dimethylformamide or the like. The cleavage is conveniently carried out at a temperature between about room temperature and the boiling point of the mixture, the latter being preferred. An especially suitable protecting group is the 2,4-dimethoxybenzyl group which is conveniently cleaved off using trifluoroacetic acid, preferably at the boiling point of the mixture.

If $R^7$ in a compound of formula XV is t-butyl, then the ester group can be hydrolyzed simultaneously under the conditions of the protecting group cleavage; there being thus obtained directly a compound of formula IV in which $R^1$ is hydrogen.

As mentioned earlier, the compounds of formula I are novel and have extremely valuable pharmacodynamic properties. They exhibit only a low toxicity and it has been shown that they have a pronounced affinity to the central benzodiazepine receptors and are capable of antagonizing the central-depressant, muscle relaxant, ataxic, blood pressure-lowering and respiratory-depressant properties of 1,4-benzodiazepines which have tranquillizing activity.

The affinity of compounds of formula I to the central benzodiazepine receptors was determined according to the method described in Life Science 20, 2101–2110 (1977) and Science 198, 849–851 (1977). According to this method, the inhibition of the binding of tritiated diazepam at the specific benzodiazepine receptors in the cerebral cortex by the respective test substances is ascertained. The $IC_{50}$ ("50% inhibiting concentration") is that concentration of the respective test substance which brings about a 50 percent inhibition of the specific binding of the tritiated diazepam at the specific benzodiazepine receptors in the cerebral cortex.

One of the typical properties of 1,4-benzodiazepines, which have tranquillizing activity, in experimental animals is their pronounced anticonvulsant activity which can be demonstrated, for example, in the known and generally recognized pentetrazole test. This property was used to evaluate the test described hereinafter which permits the determination of compounds which are capable of antagonizing the central properties of 1,4-benzodiazepines which have tranquillizing activity.

In this test, 5 mg/kg (i.p.) of diazepam (i.e. a supra-maximal dosage which in the pentetrazole test on more than 900 mice protects all experimental animals from convulsive attacks) were administered to mice 1 hour before the pentetrazole (120 mg/kg i.p.) and the compound to be tested was administered p.o. 15 minutes before the pentetrazole. The antagonistic activity of the compounds investigated, i.e. their ability to counteract the activity of the diazepam in the pentetrazole test, is determined by counting the mice which suffer convulsive attacks in this test.

In the following Table there are presented the results which have been obtained with representative members of the class of compound defined by formula I in the test previously described. The $ED_{50}$ value is given for each of the compounds listed in the Table. The $ED_{50}$ is the amount of test compound in mg/kg (p.o.) which counteracts in 50% of the animals the diazepam effect in the above test. Moreover, the Table contains the $IC_{50}$ value defined above for all test compounds listed therein as well as data concerning the acute toxicity of certain of these compounds ($LD_{50}$ in mg/kg in the case of single oral administration to mice).

TABLE

| Compound of formula I wherein | | | | | $IC_{50}$ in nM/l | $ED_{50}$ in mg/kg p.o. | $LD_{50}$ in mg/kg p.o. |
|---|---|---|---|---|---|---|---|
| A | $R^2$ | $R^3$ | $R^1$ | X | | | |
| (a) | H | Cl | —$CH_3$ | O | 3.0 | 0.2 | 312 |
| (a) | H | CN | —$CH_3$ | O | 10.0 | 1.22 | |
| (a) | H | H | —$CH_3$ | O | 3.3 | 4.7 | 625 |
| (a) | F | H | —$CH_3$ | O | 1.4 | 8.4 | |
| (a) | H | H | —$CH_3$ | S | 8.9 | 7.1 | |
| (a) | H | I | —$CH_3$ | O | 2.6 | 0.14 | |
| (a) | H | Br | —$CH_3$ | O | 2.3 | 0.13 | |

As already mentioned, the compounds of formula I antagonise the central-depressant, muscle relaxant, ataxic, blood pressure-lowering and respiratory-depressant properties of 1,4-benzodiazepines which have tranquillizing activity. The latter are in widespread use in therapy and are often administered in high dosages, so that the above-mentioned activities can also appear strongly as side-effects. The compounds of formula I can be used as antidotes in the case of intoxications in which excessive intake of 1,4-benzodiazepines which have tranquillizing activity is concerned. They are also suitable for shortening anaesthesia in surgery and in obstetrics induced by 1,4-benzodiazepines which have tranquillizing activity. In the case of neonatals, a possible respiratory depression, which deteriorates upon the administration of 1,4-benzodiazepines which have tranquillizing activity to the mother, can be counteracted. The compounds of formula I can also be used to suppress, in the case of 1,4-benzodiazepines which are used in other fields of indication, the activities on the central nervous system which are undesirable in such a case. Examples of such 1,4-benzodiazepines which can be used in other fields of indication are the schistosomicidally active, 1,4-benzodiazepines described in British patent specifications Nos. 1,444,529 and 1,474,305 such as (+)-5-(o-chlorophenyl)-1,3-dihydro-3-methyl-7-nitro-2H-1,4-benzodiazepin-2-one.

The following experiments show that a representative member of the class of substance embraced by formula I, which suppresses the strong, but undesirable, central activities of the highly active schistosomicide (+)-5-(o-chlorophenyl)-1,3-dihydro-3-methyl-7-nitro-2H-1,4-benzodiazepin-2-one on the central nervous system, is in no way detrimental to its schistosomicidal activity.

Mice and golden hamsters are infected subcutaneously with 60 cercaria of *Schistosoma mansoni*. About 42 days after the infection, they are treated orally with a single dosage of the preparation to be tested. 5 animals are used per preparation and dosage. 10 untreated animals are used as controls. The animals are killed and dissected 2 weeks (hamster) or 3 weeks (mice) after the treatment. Worm pairs in mesenteric veins, portal vein and liver are dissected-out, counted and the condition of the worms (living or dead) are registered. A schistosomicidal activity of a preparation manifests itself in the appearance of dead worms in the vessels of the liver. Dead worms are never found in untreated control animals. The test is evaluated by calculating the percentage of dead worm pairs in the liver of infected, treated animals.

In order to test the in vitro activity of preparations, worm pairs of *Schistosoma mansoni* are isolated from mice and incubated at 37° C. in a nutrient medium. Preparations are added in the form of a solution or as a suspension. The motility of the worms is observed under a microscope and registered during the test period of 120 hours. A schistosomicidal activity of a preparation manifests itself in the more or less rapid loss of motility of the worms. Control worms in the nutrient medium without the addition of a preparation maintain their normal motility during the entire test period of 120 hours.

The following representative compound of formula I was tested in the tests described above for possible detrimental effects on the schistosomicidal activity of (+)-5-(o-chlorophenyl)-1,3-dihydro-3-methyl-7-nitro-2H-1,4-benzodiazepin-2-one (compound S):
t-Butyl 7-chloro-5,6-dihydro-5-methyl-6-oxo-4H-imidazo[1,5-a][1,4]benzodiazepine-3-carboxylate (compound A).

As is evident from the following compilations relating to the results in animal tests and in the in vitro test, the schistosomicidal activity of (+)-5-(o-chlorophenyl)-1,3-dihydro-3-methyl-7-nitro-2H-1,4-benzodiazepin-2-one (compound S) was not influenced detrimentally by compound A.

| Test results in mice and hamsters: | | | | |
|---|---|---|---|---|
| Host species | Dosage in mg/kg p.o. | | Dosage ratio | Schistosomicidal activity in % |
| | Compound S | Compound A | | |
| Mouse | 75 | — | — | 100 |
| | — | 300 | — | 0 |
| | 75 | 25 | 3:1 | 100 |
| | 75 | 75 | 1:1 | 100 |

| -continued | | | | |
|---|---|---|---|---|
| Test results in mice and hamsters: | | | | |
| Host species | Dosage in mg/kg p.o. | | Dosage ratio | Schistosomicidal activity in % |
| | Compound S | Compound A | | |
| | 75 | 225 | 1:3 | 93 |
| | — | — | — | 0 |
| Hamster | 75 | — | — | 100 |
| | — | 225 | — | 0 |
| | 75 | 25 | 3:1 | 100 |
| | 75 | 75 | 1:1 | 100 |
| | 75 | 225 | 1:3 | 85 |
| | — | — | — | 0 |

| Results of the in vitro experiments: | | | |
|---|---|---|---|
| Preparation concentration in ug/ml | | Concentration ratio | Activity* |
| Compound S | Compound A | | |
| 25 | — | — | a |
| — | 100 | — | b |
| — | 25 | — | b |
| 25 | 100 | 1:4 | a |
| 25 | 25 | 1:1 | a |
| — | — | — | b |

Activity:
a = worm pairs motionless within 15 minutes;
b = worm pairs show normal motility during the test period of 120 hours.

The compounds of formula I and their pharmaceutically acceptable acid addition salts can be used as medicaments, for example in the form of pharmaceutical preparations. The pharmaceutical preparations can be administered orally (e.g. in the form of tablets, coated tablets, dragees, hard and soft gelatine capsules, solutions, emulsions or suspensions). The administration can, however, also be carried out rectally (e.g. in the form of suppositories) or parenterally (e.g. in the form of injection solutions).

For the manufacture of tablets, coated tablets, dragees and hard gelatine capsules, the compounds of formula I and their pharmaceutically acceptable acid addition salts can be processed with pharmaceutical inert, inorganic or organic carriers. Examples of such carriers which can be used for tablets, dragees and hard gelatine capsules are lactose, maize starch or derivatives thereof, talc, stearic acid or its salts etc. Suitable carriers for soft gelatine capsules are, for example, vegetable oils, waxes, fats, semi-solid and liquid polyols etc. Suitable carriers for the manufacture of solutions and syrups are, for example, water, polyols, saccharose, invert sugar, glucose and the like. Suitable carriers for injection solutions are, for example, water, alcohols, polyols, glycerine, vegetable oils etc. Suitable carriers for suppositories are, for example, natural or hardened oils, waxes, fats, semi-liquid or liquid polyols and the like.

The pharmaceutical preparations can also contain preserving agents, solubilizing agents, stabilizing agents, wetting agents, emulsifying agrnts, sweetening agents, colouring agents, flavouring agents, salts for varying the osmotic pressure, buffers, coating agents or antioxidants. They can also contain still other therepeutically valuable substances.

As mentioned earlier, compounds of formula I and pharmaceutically acceptable acid addition salts thereof can be used in accordance with the invention in the control or prevention of illnesses, especially in the antagonization of the central-depressant, muscle relaxant, ataxic, blood pressure-lowering and respiratory-depressant properties of 1,4-benzodiazepines which have tranquillizing activity. In particular, compounds of formula I can be used in combination with the schistosomicidally active compounds mentioned above, for example in combination with (+)-5-(o-chlorophenyl)-1,3-dihydro-3-methyl-7-nitro-2H-1,4-benzodiazepin-2-one, in the control of schistosomiasis. In this case, the compounds of formula I or their pharmaceutically acceptable acid addition salts can be administered before, simultaneously with or after the administration or intake of 1,4-benzodiazepines which have tranquillizing activity. If the compound of formula I or a pharmaceutically acceptable acid addition salt thereof is administered simultaneously with the 1,4-benzodiazepine which has tranquillizing activity, then this administration can be as an ad-hoc combination or in the form of a pharmaceutical combination which contains a compound of general formula I or a pharmaceutically acceptable acid addition salt thereof and a 1,4-benzodiazepine derivative which has tranquillizing activity; such pharmaceutical combinations are likewise an object of the present invention. The dosage of the compounds of formula I and their pharmaceutically acceptable acid addition salts can vary within wide limits and is, of course, fitted to the individual requirements in each particular case. In general, a daily dosage of about 0.2 mg to about 500 mg should be appropriate.

As mentioned earlier, medicaments containing a compound of formula I or a pharmaceutically acceptable acid addition salt thereof are likewise an object of the present invention as is a process for the manufacture of such medicaments which comprises bringing one or more compounds of formula I or pharmaceutically acceptable acid addition salts thereof and, if desired, one or more other therapeutically valuable substances into a galenical administration form; in this connection reference is again made to the pharmaceutical combinations mentioned above which are likewise an object of the present invention. In particular, pharmaceutical combinations containing a compound of formula I and one of the schistosomicidally-active compounds mentioned above, especially (+)-5-(o-chlorophenyl)-1,3-dihydro-3-methyl-7-nitro-2H-1,4-benzodiazepin-2-one, are an object of the present invention. Such combinations are suitable for the control of schistosomiasis.

In the following Examples, which illustrate the present invention in more detail but in no way are intended to limit its extent, all temperatures are given in degrees Centigrade.

EXAMPLE 1

(a) 29.1 g (0.14 mol) of 6-chloroisatoic acid anhydride are stirred with 13.12 g (0.14 mol) of sarcosine in 150 ml of dimethyl sulphoxide at 110° for 1 hour. The solution obtained is concentrated and the residue is recrystallized from ethanol. There is obtained 6-chloro-3,4-dihydro-4-methyl-2H-1,4-benzodiazepine-2,5(1H)-dione of melting point 237°–238°.

(b) A suspension of 0.55 g (14.2 mmol) of sodium hydride (55 percent oil dispersion) in 20 ml of dry dimethylformamide is treated with 3.18 g (14.1 mmol) of 6-chloro-3,4-dihydro-4-methyl-2H-1,4-benzodiazepine-2,5(1H)-dione. The mixture is stirred at room temperature for 1 hour, cooled to −30° and treated dropwise with 2.05 ml (14.2 mmol) of diethylchlorophosphate. The mixture is stirred at −20° for 20 minutes.

Separately, a solution of 1.59 g (14.2 mmol) of potassium t-butylate in 5 ml of dry dimethylformamide is cooled in an acetone/dry-ice bath and treated with 2.0 g (14.2 mmol) of t-butyl isocyanoacetate. The solution obtained in added dropwise at −15° to the mixture obtained according to the preceding paragraph. The cooling bath is removed and the mixture is neutralized at room temperature with 1.5 ml of glacial acetic acid. Subsequently, the mixture is poured into about 150 ml of water and extracted three times with chloroform. The organic extracts are washed four times with water, dried over magnesium sulphate and evaporated. The crude product is chromatographed on silica gel using ethyl acetate for the elution and subsequently recrystallized from ethyl acetate/ether. There is obtained t-butyl 7-chloro-5,6-dihydro-5-methyl-6-oxo-4H-imidazo[1,5-a][1,4]benzodiazepine-3-carboxylate of melting point 188°–190°.

EXAMPLE 2

(a) A suspension of 8.7 g (0.03 mol) of 6-iodoisatoic acid anhydride, 2.95 g (0.033 mol) of sarcosine and 4.2 g of potassium carbonate in 50 ml of dimethylformamide is heated to 50° for 30 minutes. After cooling, the mixture is diluted with 400 ml of water, adjusted to pH 1–2 with 2 N hydrochloric acid and extracted several times with chloroform/isopropanol (4:1). After evaporation of the solvent and recrystallization of the residue from methylene chloride/hexane, there is obtained N-(6-iodoanthraniloyl)-N-methylglycine of melting point 147°–149°.

(b) 4.6 g of the compound obtained according to paragraph (a) are heated to 160° for about 10 minutes. The water formed during the heating is removed in vacuo and the crude product is recrystallized from methylene chloride/hexane. There is obtained 3,4-dihydro-6-iodo-4-methyl-2H-1,4-benzodiazepine-2,5(1H)-dione of melting point 217°–220°.

(c) A suspension of 0.28 g (6.6 mmol) of sodium hydride (55 percent oil dispersion) in 10 ml of dry dimethylformamide is treated with 1.94 g (6.1 mmol) of 3,4-dihydro-6-iodo-4-methyl-2H-1,4-benzodiazepine-2,5(1H)-dione. After 30 minutes, the mixture is cooled to −35° and treated dropwise with 1.1 ml (6.6 mmol) of diethylchlorophosphate. Subsequently, the mixture is stirred at −35° to −15° for about a further 15 minutes.

Separately, a solution of 0.72 g (6.6 mmol) of potassium t-butylate in 4 ml of dry dimethylformamide is cooled in an acetone/dry-ice bath and treated with 0.95 g (6.6 mmol) of t-butyl isocyanoacetate. The solution obtained is added dropwise at −15° to −5° to the mixture obtained according to the preceding paragraph. The cooling bath is removed, the mixture is neutralized after about 15 minutes with glacial acetic acid, poured into 100 ml of water and extracted three times with chloroform. The chloroform extracts are washed three times with water, dried over magnesium sulphate and evaporated. The purification of the crude product is carried out by chromatography on a silica gel column and subsequent recrystallization from ethyl acetate. There is obtained t-butyl 5,6-dihydro-7-iodo-5-methyl-6-oxo-4H-imidazo[1,5-a][1,4]benzodiazepine-3-carboxylate of melting point 203°–204°.

EXAMPLE 3

(a) A mixture of 8.7 g (0.03 mol) of 6-iodoisatoic acid anhydride, 3.2 g (0.036 mol) of sarcosine and 25 ml of dimethylacetamide is heated to boiling under reflux for 1 hour. After cooling and dilution with water, the mixture is extracted with chloroform. The chloroform extracts are dried and evaporated. After recrystallization of the crude product from methylene chloride/ether, there is obtained 3,4-dihydro-6-iodo-4-methyl-2H-1,4-benzodiazepine-2,5(1H)-dione of melting point 214°–217°.

(b) In analogy to the details of Example 2c, from the compound obtained according to paragraph (a) there is obtained t-butyl 5,6-dihydro-7-iodo-5-methyl-6-oxo-4H-imidazo[1,5-a][1,4]benzodiazepine-3-carboxylate of melting point 203°–204°.

EXAMPLE 4

(A) A mixture of 5.7 g (0.018 mol) of 3,4-dihydro-6-iodo-4-methyl-2H-1,4-benzodiazepine-2,5(1H)-dione, 2.4 g (0.026 mol) of copper (I) cyanide and 60 ml of dimethylformamide is heated to 50° for 45 minutes. After cooling, the mixture is diluted with water and extracted several times with chloroform/isopropanol (4:1). The combined organic extracts are dried over magnesium sulphate and evaporated. The yellow-brown crude product is recrystallized from methanol, there being obtained 2,3,4,5-tetrahydro-4-methyl-2,5-dioxo-1H-1,4-benzodiazepine-6-carbonitrile of melting point 253–256.

(b) A suspension of 0.31 g (7.2 mmol) of sodium hydride (55 percent oil dispersion) in 8 ml of dry dimethylformamide is treated with 1.3 g (6.0 mmol) of 2,3,4,5-tetrahydro-4-methyl-2,5-dioxo-1H-1,4-benzodiazepine-6-carbonitrile. After about 30 minutes, the mixture is cooled to −35°, treated dropwise with 1.2 ml (7.2 mmol) of diethylchlorophosphate and stirred at −35° to −15° for 15 minutes.

Separately, a solution of 0.79 g (7.2 mmol) of potassium t-butylate in 3 ml of dry dimethylformamide is cooled in an acetone/dry-ice bath and treated with 1.01 g (7.2 mmol) of t-butyl isocyanoacetate. The solution obtained is added dropwise at −15° to −10° to the mixture obtained according to the preceding paragraph. The cooling bath is removed, the mixture is neutralized after about 10 minutes with glacial acetic acid, poured into 100 ml of water and extracted three times with chloroform. The chloroform extracts are washed with water, dried over magnesium sulphate and evaporated. The crude product is chromatographed on silica gel using chloroform containing 1.5% methanol for the elution and subsequently recrystallized from ethyl acetate. There is obtained t-butyl 7-cyano-5,6-dihydro-5-methyl-6-oxo-4H-imidazo[1,5-a][1,4]benzodiazepine-3-carboxylate of melting point 213°–215°.

EXAMPLE 5

A suspension of 0.55 g (14.2 mmol) of sodium hydride (55 percent oil dispersion) in 15 ml of dry dimethylformamide is treated with 2.69 g (14.16 mmol) of 3,4-dihydro-4-methyl-2H-1,4-benzodiazepine-2,5(1H)-dione and the mixture is stirred at room temperature for 1 hour. Subsequently, the mixture is cooled to −30°, treated dropwise with 2.05 ml (14.2 mmol) of diethylchlorophosphate and stirred at −20° for 20 minutes.

Separately, a solution of 1.59 g (14.2 mmol) of potassium t-butylate in 5 ml of dry dimethylformamide is cooled in an acetone/dry-ice bath and treated with 2.0 g (14.2 mmol) of t-butyl isocyanoacetate. The solution obtained is added dropwise at −15° to the mixture obtained according to the preceding paragraph. The cooling bath is removed, the mixture is neutralized at room temperature with 1.5 ml of glacial acetic acid, poured into about 100 ml of water and extracted three times with chloroform. The chloroform extracts are washed four times with water, dried over magnesium sulphate and evaporated. The crude product is purified by chromatography on a silica gel column using ethyl acetate for the elution and subsequent recrystallization from ethyl acetate/ether. There is obtained t-butyl 5,6-dihydro-5-methyl-6-oxo-4H-imidazo[1,5-a]benzodiazepine-3-carboxylate of melting point 217°–218°.

EXAMPLE 6

1 g of t-butyl 5,6-dihydro-5-methyl-6-oxo-4H-imidazo[1,5-a][1,4]benzodiazepine-3-carboxylate in 50 ml of toluene is treated with 0.82 g of 2,4-bis(p-methoxyphenyl)-1,3,2,4-dithiadiphosphetane-2,4-disulphide and the mixture obtained is heated to boiling under reflux for 6 hours. The mixture is poured into water and the toluene phase is separated. After drying the organic phase over magnesium sulphate and evaporation, the crude product is chromatographed on silica gel. There is obtained t-butyl 5,6-dihydro-5-methyl-6-thioxo-4H-imidazo[1,5-a][1,4]benzodiazepine-3-carboxylate on melting point 207°–208°.

EXAMPLE 7

(a) 24 g (132.5 mmol) of 5-fluoroisatoic acid anhydride are dissolved in 140 ml of dimethyl sulphoxide and treated with 11.8 g (132.5 mmol) of sarcosine. The solution is stirred at 100° until the gas evolution ceases (duration: about 1.5 hours) and subsequently poured into about 1.2 l of water. After stirring for 10 minutes, a solid material crystallizes out. The crystals are filtered off under suction, washed with 1 l of water and dried. There is obtained 7-fluoro-3,4-dihydro-4-methyl-2H-1,4-benzodiazepine-2,5(1H)-dione of melting point 262°–263°.

(b) A solution of 10.40 g (50 mmol) of 7-fluoro-3,4-dihydro-4-methyl-2H-1,4-benzodiazepine-2,5(1H)-dione in 50 ml of dry dimethylformamide is treated under an argon atmosphere with 1.92 g (50 mmol) of sodium hydride (50 percent oil dispersion) and the mixture is stirred at room temperature for 20 minutes. Subsequently, at −20° there are added dropwise thereto 8.62 g (50 mmol) of diethylchlorophosphate and the mixture is stirred at −20° for a further 20 minutes.

Separately, a solution of 5.60 g (50 mmol) of potassium t-butylate in 15 ml of dimethylformamide is cooled in an acetone/dry-ice bath and treated with 7.0 g (50 mmol) of t-butyl isocyanoacetate. The orange solution obtained is added dropwise at −10° to −20° to the mixture obtained according to the preceding paragraph. The cooling bath is removed. The mixture is stirred for 20 minutes, neutralizing with 5 ml of glacial acetic acid, poured into water and extracted three times with chloroform. The combined organic extracts are washed five times with water, dried over magnesium sulphate and evaporated. After recrystallization from ethyl acetate, there is obtained t-butyl 8-fluoro-5,6-dihydro-5-methyl-6-oxo-4H-imidazo[1,5-a][1,4]benzodiazepine-3-carboxylate of melting point 228°–229°.

EXAMPLE 8

(a) 19.0 g (0.10 mol) of 3,4-dihydro-4-methyl-2H-1,4-benzodiazepine-2,5(1H)-dione are placed in 100 ml of dry dimethylformamide under an argon atmosphere. 15.5 g (0.12 mol) of potassium t-butylate are added thereto, the temperature rising from 25° to 39°. The mixture is cooled to room temperature and 18.2 g (0.105 mol) of diethylchlorophosphate are added dropwise thereto between 18° to 22°.

Separately, 11.2 g (0.10 mol) of potassium t-butylate are dissolved in 30 ml of dimethylformamide. This solution is cooled to about −50° and treated under argon with 11.3 g (0.10 mol) of ethyl isocyanoacetate. Subsequently, this solution is added dropwise at 18° to 23° while cooling to the mixture obtained according to the preceding paragraph. The mixture is stirred at room temperature for 1 hour, 5 ml of acetic acid are added thereto, the mixture is then poured into 500 ml of water and extracted twice with 200 ml of chloroform each time. The combined chloroform extracts are washed three times with 300 ml of water each time, dried over magnesium sulphate and evaporated. 150 ml of ethyl acetate are added to the oily residue and it is left to crystallize at 0°. The separated crystals are filtered off under suction and washed with cold ethyl acetate, there being obtained ethyl 5,6-dihydro-5-methyl-6-oxo-4H-imidazo[1,5-a][1,4]benzodiazepine-3-carboxylate of melting point 163°–165°. After recrystallization from ethyl acetate, this product has a melting point of 164°–165°.

(b) A solution of 14.26 g (0.05 mol) of ethyl 5,6-dihydro-5-methyl-6-oxo-4H-imidazo[1,5-a][1,4]benzodiazepine-3-carboxylate and 2.2 g (0.055 mol) of sodium hydroxide in 100 ml of ethanol and 20 ml of water is heated to boiling under reflux for 45 minutes and subsequently treated with 55 ml of 1 N hydrochloric acid and 50 ml of water. After distillation of the ethanol, the resulting crystal slurry is filtered off under suction, washed with water and dried. There is obtained 5,6-dihydro-5-methyl-6-oxo-4H-imidazo[1,5-a][1,4]benzodiazepine-3-carboxylic acid of melting point 287°.

(c) A suspension of 2.6 g (10 mmol) of 5,6-dihydro-5-methyl-6-oxo-4H-imidazo[1,5-a][1,4]benzodiazepine-3-carboxylic acid in 20 ml of pyridine is firstly treated with 25 ml of t-butanol and subsequently treated dropwise at −5° with 1.1 ml of phosphorus oxychloride. The mixture is stirred at −5° for 15 minutes and at room temperature for 48 hours, poured into 250 ml of water and extracted four times with chloroform. The chloroform extracts are washed three times with dilute sodium hydroxide and three times with water, dried over magnesium sulphate and evaporated. After recrystallization of the residue from ethyl acetate, there is obtained t-butyl 5,6-dihydro-5-methyl-6-oxo-4H-imidazo[1,5-a][1,4]benzodiazepine-3-carboxylate of melting point 216°–217°.

EXAMPLE 9

(a) 4.84 g (0.02 mol) of 6-bromoisatoic acid anhydride and 1.78 g (0.02 mol) of sarcosine are finely rubbed together and subsequently heated to 260° under a protective gas for 6 minutes. After cooling, the crude product is chromatographed on silica gel using chloroform/methanol (20:1) for the elution. After recrystallization from chloroform/hexane, there is obtained 6-bromo-3,4-dihydro-4-methyl-2H-1,4-benzodiazepine-2,5(1H)-dione of melting point 232°–233°.

(b) A suspension of 0.98 g (22.4 mmol) of sodium hydride (55 percent oil dispersion) in 35 ml of dry dimethylformamide is treated with 5.26 g (19.5 mmol) of 6-bromo-3,4-dihydro-4-methyl-2H-1,4-benzodiazepine-2,5(1H)-dione and stirred at room temperature for 45 minutes. Subsequently, 3.3 ml (22.4 mmol) of diethylchlorophosphate are added dropwise to the mixture and the resulting mixture is stirred at room temperature for a further 25 minutes.

Separately, a solution of 2.62 g (23.4 mmol) of potassium t-butylate in 6 ml of dry dimethylformamide is cooled in an acetone/dry-ice bath, treated with 3.38 g (23.4 mmol) of t-butyl isocyanoacetate and added dropwise at −15° to the mixture obtained according to the preceding paragraph. The cooling bath is removed, the mixture is stirred until the internal temperature has reached 5°, neutralized with glacial acetic acid, poured into 200 ml of water and extracted four times with methylene chloride. The methylene chloride extracts are washed three times with water, dried over magnesium sulphate and evaporated. The crude product is chromatographed on silica gel using ethyl acetate/methylene chloride (1:1) for the elution and subsequently recrystallized twice from ethyl acetate. There is obtained t-butyl 7-bromo-5,6-dihydro-5-methyl-6-oxo-4H-imidazo[1,5-a][1,4]benzodiazepine-3-carboxylate of melting point 207°–208°.

EXAMPLE 10

A mixture of 5.02 g (22.7 mmol) of 6-chloro-3,4-dihydro-4-methyl-2H-1,4-benzodiazepine-2,5(1H)-dione, 31.5 g (260 mmol) of dimethylaniline, 5.20 g (34 mmol) of phosphorus oxychloride and 50 ml of chloroform (filtered over aluminium oxide) is stirred at the boiling point for 2 hours. The solution obtained is poured into a pre-cooled mixture of 18 g of sodium bicarbonate and 100 ml of water and stirred for 20 minutes. The inorganic phase is separated and extracted three times with chloroform. The combined chloroform extracts are dried over magnesium sulphate and evaporated in a high vacuum. The crystalline residue (iminochloride) is dissolved in 30 ml of dimethylformamide.

Separately, a solution of 2.63 g (23.5 mmol) of potassium t-butylate in 10 ml of dimethylformamide is cooled to −40°, treated firstly with 3.22 g (22.9 mmol) of t-butyl isocyanoacetate and subsequently dropwise at −10° to −20° with the solution of the imino chloride obtained according to the preceding paragraph. The cooling is removed, the mixture is stirred for 0.5 hour, treated with 2.5 ml of glacial acetic acid, poured into about 200 ml of water and extracted four times with about 40 ml of chloroform each time. The combined chloroform extracts are washed three times with water, dried over magnesium sulphate and evaporated. The crude product is recrystallized from ethyl acetate/ether and yields t-butyl 7-chloro-5,6-dihydro-5-methyl-6-oxo-4H-imidazo[1,5-a][1,4]benzodiazepine-3-carboxylate of melting point 194°–196°.

EXAMPLE A

Tablets containing the following ingredients are manufactured:

|  | mg/tablet |
|---|---|
| t-Butyl 7-chloro-5,6-dihydro-5-methyl-6-oxo-4H-imidazo[1,5-a] [1,4] benzodiazepine-3-carboxylate | 1 |

| | mg/tablet |
|---|---|
| Lactose | 103 |
| Maize starch | 25 |
| Microcrystalline cellulose | 70 |
| Magnesium stearate | 1 |
| Total | 200 |

EXAMPLE B

Capsules containing the following ingredients are manufactured:

| | mg/capsule |
|---|---|
| t-Butyl 5,6-dihydro-7-iodo-5-methyl-6-oxo-4H-imidazo[1,5-a] [1,4] benzodiazepine-3-carboxylate | 1 |
| Lactose | 164 |
| Maize starch | 30 |
| Talc | 5 |
| Total | 200 |

The active substance, lactose and maize starch are firstly mixed in a mixer and then in a comminuting machine. The mixture is returned to the mixer, the talc is added thereto and mixed thoroughly. The mixture is filled by machine into hard gelatine capsules.

EXAMPLE C

Injection solutions containing the following ingredients are manufactured:

| | Per ml | |
|---|---|---|
| t-Butyl 7-bromo-5,6-dihydro-5-methyl-6-oxo-4H-imidazo[1,5-a] [1,4] benzodiazepine-3-carboxylate | 0.5 | mg |
| Propyleneglycol | 0.4 | ml |
| Ethanol (95 percent) | 0.1 | ml |
| Sodium benzoate | 48.8 | mg |
| Benzyl alcohol | 0.015 | ml |
| Benzoic acid | 1.2 | mg |
| Water for injection q.s. ad | 1.0 | |

For the manufacture of 10 000 ml of injection solution, 5 g of the active substance are dissolved in 150 ml of benzyl alcohol and 4000 ml of propyleneglycol and 1000 ml of ethanol are added thereto. Then, 12 g of benzoic acid are dissolved in the above mixture and there is added thereto a solution of 488 g of sodium benzoate in 300 ml of water for injection. The solution obtained is made up to a volume of 10 000 ml by adding water for injection, filtered and filled into ampoules of suitable size; the residual volume of the ampoules is filled with nitrogen, the ampoules are sealed and sterilized for 30 minutes in an autoclave at 0.7 atmospheres.

EXAMPLE D

Suppositories containing the following ingredients are manufactured:

| | g/supp. |
|---|---|
| t-Butyl 7-chloro-5,6-dihydro-5-methyl-6-oxo-4H-imidazo[1,5-a] [1,4] benzodiazepine-3-carboxylate | 0.001 |
| Cocoa butter (m.p. 36–37°) | 1.255 |
| Carnauba wax | 0.044 |
| Total | 1.3 |

The cocoa butter and carnauba wax are melted in a glass or steel vessel, mixed thoroughly and cooled to 45°. Thereupon, there is added thereto the finely powdered active substance and the mixture is stirred until it is completely dispersed. The mixture is poured into suppository moulds of suitable size, left to cool, the suppositories are then removed from the moulds and packed individually in wax paper or metal foil.

EXAMPLE E

Capsules containing the following ingredients are manufactured:

| | mg/capsule |
|---|---|
| (+)-5-(o-Chlorophenyl)-1,3-dihydro-3-methyl-7-nitro-2H-1,4-benzodiazepin-2-one | 30.0 |
| t-Butyl 7-chloro-5,6-dihydro-5-methyl-6-oxo-4H-imidazo[1,5-a] [1,4] benzodiazepine-3-carboxylate | 20.0 |
| Lactose (crystalline) | 100.0 |
| Maize starch (white) | 27.5 |
| Talc | 10.0 |
| Magnesium stearate | 2.5 |
| Total | 190.0 |

The two active substances are mixed well with the adjuvants and 190.0 mg of the mixture are filled into interlocking capsules of suitable size.

EXAMPLE F

Tablets containing the following ingredients are manufactured:

| | mg/tablet |
|---|---|
| (+)-5-(o-Chlorophenyl)-1,3-dihydro-3-methyl-7-nitro-2H-1,4-benzodiazepin-2-one | 30.0 |
| t-Butyl 7-bromo-5,6-dihydro-5-methyl-6-oxo-4H-imidazo[1,5-a] [1,4] benzodiazepine-3-carboxylate | 10.0 |
| Lactose (powdered) | 15.0 |
| Maize starch (white) | 19.5 |
| Povidon K30 | 3.5 |
| Maize starch (white) | 10.0 |
| Magnesium stearate | 2.0 |
| Total | 90.0 |

The two active substances, the powdered lactose and the first portion of white maize starch are mixed and sieved. This mixture is moistened with a solution of the Povidon K30 in water, kneaded, granulated, dried and sieved. The second portion of white maize starch and the magnesium stearate are added to the granulate. After mixing, the mass obtained is pressed to tablets weighing 90 mg.

EXAMPLE G

Tablets containing the following ingredients are manufactured:

| | mg/tablet |
|---|---|
| (+)-5-(o-Chlorophenyl)-1,3-dihydro-3-methyl-7-nitro-2H-1,4-benzodiazepin-2-one | 30 |

| | mg/tablet |
|---|---|
| t-Butyl 5,6-dihydro-7-iodo-5-methyl-6-oxo-4H-imidazo[1,5-a] [1,4] benzodiazepine-3-carboxylate | 30 |
| Lactose (powdered) | 22 |
| Maize starch (white) | 22 |
| Povidon K30 | 6 |
| Maize starch (white) | 16 |
| Magnesium stearate | 4 |
| Total | 130 |

The two active substances, the powdered lactose and the first portion of white maize starch are mixed and sieved. This mixture is moistened with a solution of the Povidon K30 in water, kneaded, granulated, dried and sieved. The second portion of white maize starch and the magnesium stearate are added to the granulate. After mixing, the mass obtained is pressed to tablets weighing 130 mg.

What is claimed:

1. A compound of the formula

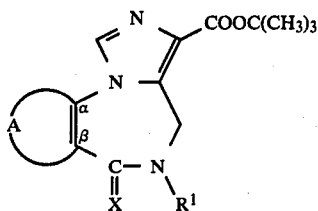

wherein A together with the two carbon atoms denoted as α and β is the group

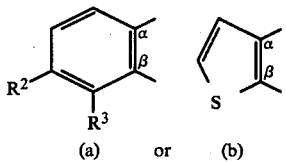

X is an oxygen or sulphur atom and $R^1$ is hydrogen or lower alkyl, and either $R^2$ is hydrogen, trifluoromethyl, halogen, cyano or nitro and $R^3$ is hydrogen or $R^2$ is hydrogen and $R^3$ is trifluoromethyl, halogen, cyano, nitro or lower alkyl, and pharmaceutically acceptable acid addition salts thereof.

2. The compound of claim 1, wherein A is group (a).

3. The compound of claim 2, wherein either $R^2$ is hydrogen or fluorine and $R^3$ is hydrogen, or $R^2$ is hydrogen and $R^3$ is chlorine, bromine, iodine or cyano.

4. The compound of claim 3, wherein X is an oxygen atom.

5. The compound of claim 4, wherein $R^1$ is methyl.

6. The compound: t-Butyl 7-chloro-5,6-dihydro-5-methyl-6-oxo-4H-imidazo[1,5-a][1,4]benzodiazepine-3-carboxylate.

7. The compound: t-Butyl 5,6-dihydro-7-iodo-5-methyl-6-oxo-4H-imidazo[1,5-a][1,4]benzodiazepine-3-carboxylate.

8. The compound: t-Butyl 7-bromo-5,6-dihydro-5-methyl-6-oxo-4H-imidazo[1,5-a][1,4]benzodiazepine-3-carboxylate.

9. A compound selected from the group consisting of t-Butyl 7-cyano-5,6-dihydro-5-methyl-6-oxo-4H-imidazo[1,5-a][1,4]benzodiazepine-3-carboxylate, t-butyl 5,6-dihydro-5-methyl-6-oxo-4H-imidazo[1,5-a][1,4]benzodiazepine-3-carboxylate, t-butyl 5,6-dihydro-5-methyl-6-thioxo-4H-imidazo[1,5-a][1,4]benzodiazepine-3-carboxylate or t-butyl 8-fluoro-5,6-dihydro-5-methyl-6-oxo-4H-imidazo[1,5a][1,4]benzodiazepine-3-carboxylate.

10. A method of antagonizing, in a patient, the central-depressant, muscle relaxant, ataxic, blood pressure-lowering and respiratory-depressant properties of 1,4-benzodiazepines which have tranquillizing activity which comprises daily administering to said patient from about 0.2 mg to about 500 mg of a compound of the formula

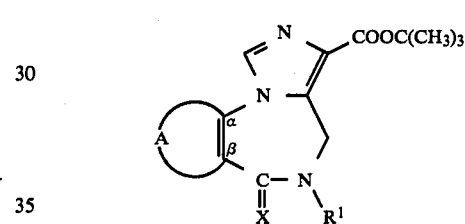

wherein A together with the two carbon atoms denoted as α and β is the group

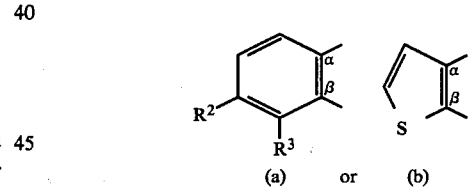

X is an oxygen or sulphur atom and $R^1$ is hydrogen or lower alkyl, and either $R^2$ is hydrogen, trifluoromethyl, halogen, cyano or nitro and $R^3$ is hydrogen or $R^2$ is hydrogen and $R^3$ is trifluoromethyl, halogen, cyano, nitro or lower alkyl, or the pharmaceutically acceptable acid addition salts thereof.

11. The method of claim 10 wherein the 1,4-benzodiazepine also has activity against schistosomiasis.

* * * * *